(12) United States Patent
Masaki et al.

(10) Patent No.: US 11,571,268 B1
(45) Date of Patent: Feb. 7, 2023

(54) MEDICAL CONTINUUM ROBOT EXTRACTION AND METHODS THEREOF

(71) Applicant: Canon U.S.A., Inc., Melville, NY (US)

(72) Inventors: Fumitaro Masaki, Cambridge, MA (US); Brian Ninni, Brighton, MA (US); Takahisa Kato, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 407 days.

(21) Appl. No.: 16/833,192

(22) Filed: Mar. 27, 2020

Related U.S. Application Data

(60) Provisional application No. 62/828,250, filed on Apr. 2, 2019.

(51) Int. Cl.
| | |
|---|---|
| *A61B 34/20* | (2016.01) |
| *A61B 34/37* | (2016.01) |
| *A61B 34/00* | (2016.01) |
| *A61B 1/005* | (2006.01) |
| *A61B 1/00* | (2006.01) |
| *A61B 1/267* | (2006.01) |
| *A61B 90/00* | (2016.01) |
| *A61B 34/30* | (2016.01) |

(52) U.S. Cl.
CPC .......... *A61B 34/74* (2016.02); *A61B 34/25* (2016.02); *A61B 34/37* (2016.02); *A61B 90/06* (2016.02); *A61B 2034/301* (2016.02); *A61B 2034/742* (2016.02); *A61B 2090/062* (2016.02); *A61B 2090/064* (2016.02); *A61B 2090/067* (2016.02); *A61B 2562/02* (2013.01)

(58) Field of Classification Search
CPC .............................. A61B 34/74; A61B 34/25
See application file for complete search history.

(56) References Cited

U.S. PATENT DOCUMENTS

| | | | | |
|---|---|---|---|---|
| 4,873,965 A | * | 10/1989 | Danieli ............... | A61B 1/0055 600/152 |
| 4,911,148 A | * | 3/1990 | Sosnowski ......... | A61B 1/00165 600/164 |
| 4,947,827 A | * | 8/1990 | Opie .................. | A61B 1/00073 600/149 |
| 5,829,444 A | * | 11/1998 | Ferre .................. | A61B 5/064 128/897 |
| 6,175,756 B1 | * | 1/2001 | Ferre .................. | A61B 90/36 606/130 |
| 6,190,395 B1 | * | 2/2001 | Williams ............ | A61B 34/20 606/130 |
| 8,052,695 B2 | * | 11/2011 | Kienzle, III ........ | A61B 34/20 606/130 |
| 2012/0059248 A1 | | 3/2012 | Holsing et al. | |
| 2015/0245874 A1 | * | 9/2015 | Hatta ................. | A61B 34/77 700/257 |

OTHER PUBLICATIONS

Choset, H., et al., "A Follow-the-Leader Approach to Serpentine Robot Motion Planning" J. Aerosp. Eng., 1999, vol. 12, No. 2.

* cited by examiner

*Primary Examiner* — Christian A Sevilla
(74) *Attorney, Agent, or Firm* — Canon U.S.A., Inc. IIP Division

(57) ABSTRACT

The subject disclosure is directed to an articulated medical device having a sensor for detecting outside movements applied upon the medical device while in a subject or patient, wherein the device is capable of maneuvering within the subject or patient while taking the outsides movements into consideration.

18 Claims, 3 Drawing Sheets

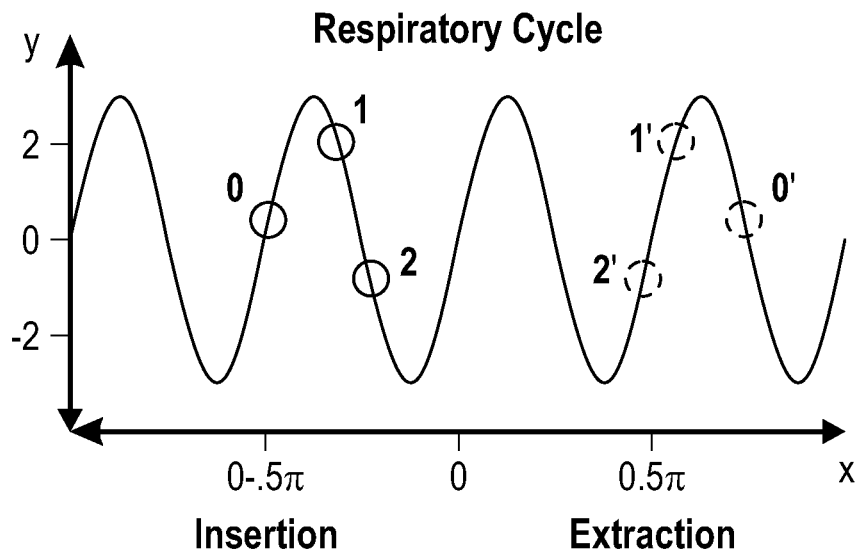
FIG. 1A
History
| # | Insertion Depth | Input Angle | Respiratory Phase |
|---|---|---|---|
| 0 | 0 | 8 | $\pi/10$ |
| 1 | 5 | 15 | $\pi/3$ |
| 2 | 10 | 18 | $2\pi/3$ |
| --- Switch From Insertion to Extraction--- | | | |
| 2' | 10 | 18 | $2\pi/3$ |
| 1' | 5 | 15 | $\pi/3$ |
| 0' | 0 | 8 | $\pi/10$ |
FIG. 1B
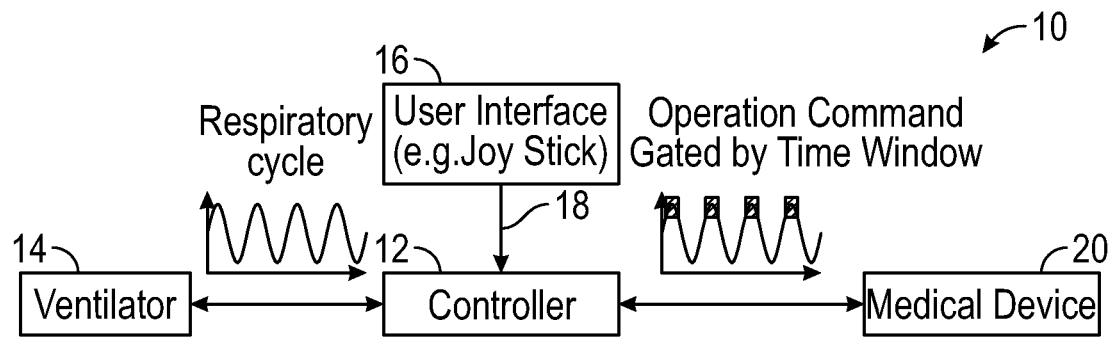
FIG. 2

MEDICAL CONTINUUM ROBOT EXTRACTION AND METHODS THEREOF

CROSS REFERENCE TO RELATED PATENT APPLICATIONS

This application claims priority from U.S. Provisional Patent Application No. 62/828,250 filed on Apr. 2, 2019, in the United States Patent and Trademark Office, the disclosure of which is incorporated herein in its entirety by reference.

FIELD OF DISCLOSURE

The present disclosure relates generally to an articulated medical apparatus having a hollow cavity, wherein the apparatus is capable of maneuvering within a subject/patient, and allowing a medical tool to be guided through the hollow cavity for medical procedures, including endoscopes, cameras, and catheters. More specifically, the subject disclosure details a medical apparatus and methods for extracting the medical apparatus through the ever-changing anatomy of a subject/patient.

BACKGROUND OF THE DISCLOSURE

Articulated medical devices generally include one or more channels that extend along the inside of the device to allow access to end effectors (the actual working part of a surgical instrument or tool) located at a distal end of the medical device. Control mechanisms located at a proximal end of the medical device are configured to enable remote manipulation of the end effectors via the one or more channels. Accordingly, the mechanical structure of the medical device plays a key role in ensuring flexible access to end effectors, while protecting delicate organs and tissues of a patient.

In order to facilitate articulation of these medical devices, continuum robots are used in clinical cases, especially to articulate around/through organs with tortuous structures, such as the airway of the lung and blood vessel. Clinical studies have shown that robotic bronchoscope can reach higher generation of the airway of the lung than a conventional manual bronchoscope. In addition, a navigation bronchoscopy system which combines electromagnetic navigation system with respiratory gating technology. This system displays the shape of the airway based on respiratory motion.

In order to control a continuum robot with multiple articulating sections, follow-the-leader ("FTL") motion is widely used. In FTL, an operator only controls the leading section of the continuum robot, allowing and the rest of articulating sections to automatically follow the path of the leading section.

By way of example United Stated Patent Application no. 2012/0059248 to Holsing et al. details a pathway process wherein the respiratory signal is used to gate localization data of the instrument to determine on airway models and correlate the instrument position to the image data to provide a registration of the patient airway models during a respiratory cycle of the patient.

However, the existing art fails to address a relevant and challenging element of the continuum robot process, namely, the extraction of the robot in a live, moving patient. More specifically, as breathing motion, or other voluntary and involuntary motions of a patient, alter the shape of airway between insertion and extraction of the continuum robot, the extraction route may be significantly varied from the insertion route.

Furthermore, breathing motion decreases the advantage of FTL, in that FTL assumes that the shape of surroundings remains constant. However, when following section(s) follow the tip section of the medical device, breathing motion changes the shape of the airway. As such, the following section may make contact with the differing shape of the anatomy.

Accordingly, extraction may cause abrasion or trauma to the airway, or other inner elements of the patient, if the shape of airway is altered.

SUMMARY

Thus, to address such exemplary needs in the industry, the present disclosure teaches apparatus, systems and methods for insertion and extraction of a medical apparatus, wherein the medical apparatus comprises: a driving unit; a single sheath that includes a first bendable segment and a second bendable segment, which are bendable by the driving unit; a controller configured to send a control signal to the driving unit for bending the at least two bendable segments; and a device for measuring a movement in a subject.

In various embodiments, the medical apparatus further comprising a sensor configured in the single sheath for measuring a value selected from the group consisting of insertion depth, input angle, movement and force upon the sheath.

In other embodiments, the medical apparatus device may be in communication with the controller for identifying variations or patterns of movement in the subject.

In further embodiment, the device for measuring movement is configured to measure voluntary or involuntary movement in the subject.

In yet additional embodiments, the movement measured in the subject is selected from the group consisting of respiration, digestion, blood circulation, and enzyme production/distribution.

Furthermore, the movement measured in the subject may be accomplished by a position sensor, flow meter, or other measuring devices known in the art, which may be placed within, affixed to, or near the subject.

It is further envisioned that the controller 12 is configured to control the first bendable segment independent of the second bendable segment, while a force is applied from the controller 12 to the second bendable segment via the driving unit in order to maintain a shape of the second bendable segment.

In yet additional embodiments, the first bendable segment and the second bendable segment are configured to independently change a respective bending angle and a respective bending plane in a three dimension space.

Furthermore, the controller 12 is configured to dislocate from the sheath at a distal end of the sheath. In addition, the sheath may further comprise an outer wall covering at least the first bendable segment. In addition, the outer wall may be configured to attach to the first bendable segment and provide flexible support to the sheath.

In yet additional embodiments, the sheath comprises a hollow cavity extending the length of the sheath for insertion of a medical tool, wherein the medical tool may be selected from the group consisting of an endoscopes, a camera, a catheter, clamps, a grasper, scissors, staplers, a needle holder, variations thereof, and derivatives therefrom.

Furthermore, the subject disclosure also teaches a method for treating a subject, comprising: a medical apparatus comprising: a driving unit; a single sheath that includes a first bendable segment and a second bendable segment, which are bendable by the driving unit; a controller configured to send a control signal to the driving unit for bending the at least two bendable segments; and a device for measuring a movement in a subject, the method including: inserting the medical apparatus into the subject; measuring the movements of a subject while employing the medical device; recording the movements; and removing the medical apparatus from the subject, wherein the recorded movements are considered when removing the medical device.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

FIG. 1A illustrates a respiratory cycle of a subject/patient, according to one or more embodiments of the present subject matter.

FIG. 1B is a chart depicting a respiratory cycle of a subject/patient, according to one or more embodiments of the present subject matter.

FIG. 2 provides a diagram of the communication of at least two elements of a medical apparatus, according to one or more embodiments of the present subject matter.

Figure 3:
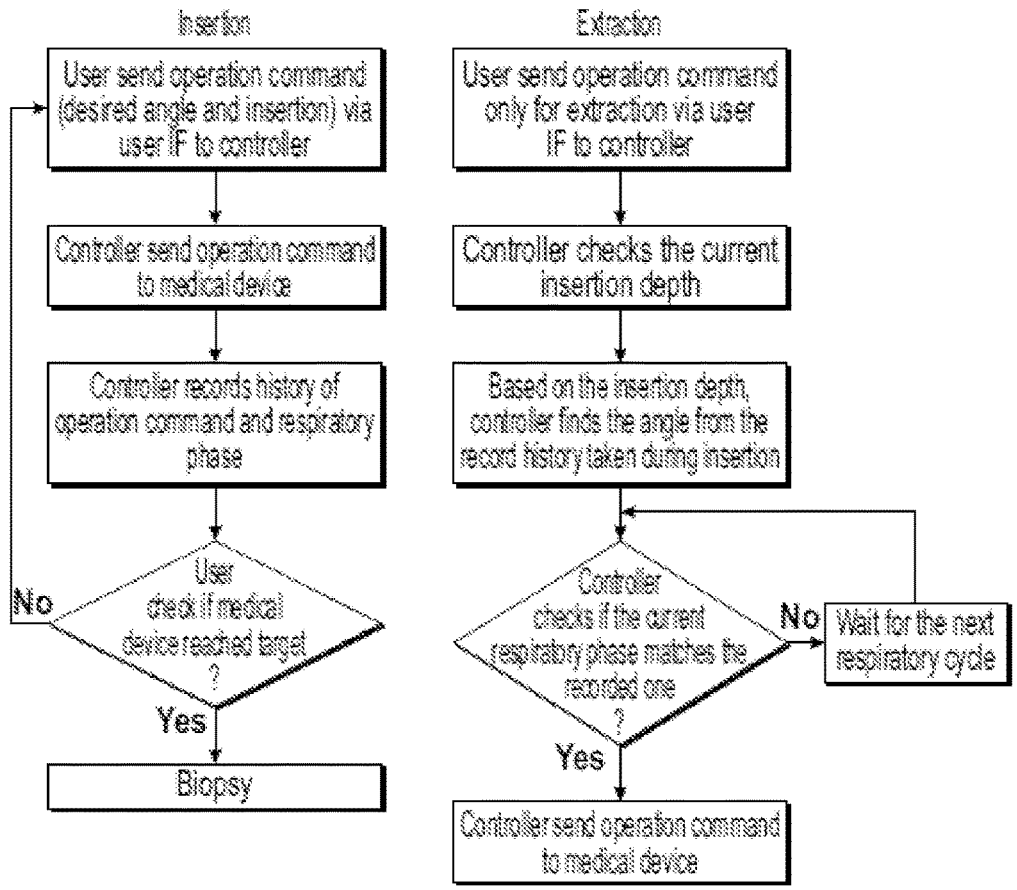
FIG. 3 is a flow chart of a continuum robot insertion and extraction method, according to one or more embodiments of the present subject matter.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

The present subject matter discloses apparatus, systems and methods for an articulated medical device configured to be guided into a patient or subject (hereafter used interchangeably) and articulated around/through organs and other elements within the patient to reach a desired destination. The medical apparatus is designed to navigate through tortuous structures without causing harm or trauma to the patient, as well as being capable of non-evasive extraction from the patient, even after the patient has moved.

By incorporating a mechanism to monitor and/or record various movements in the patient, the present subject matter can take those recordings into account when extracting the medical device. Although respiratory movement has been focused on in the subject disclosure, any voluntary or involuntary movements in the patient may be accounted for, and adjusted accordingly, when the medical device is being extracted. Examples of movement in the patient which may be accounted for by the subject innovation include, but are not limited to, respiration, digestion, blood circulation, or enzyme production/distribution.

In order to retract the medical device (also referred to as a "continuum snake" or "snake") 20 safely, a controller 12 records the breathing motion (respiratory phase) of the patient, the insertion depth of medical device 20, and the input angle of the medical device 20 during insertion. FIG. 1A is an exemplary cycle of breathing for a given patient, wherein the markers "0", "1", and "2" signify moments in a respiratory phase during insertion of the medical device 20, and markers "0'", "1'", and "2'" signify corresponding moments to markers "0", "1", and "2", respectfully, signify moments in a respiratory phase during extraction.

With respect to FIG. 1B, the recorded insertion depth of the medical device 20, and the input angle of the medical device 20 is recorded in a chart. The respiratory phase is also depicted. Upon moving from insertion of the medical device 20 to extraction of the medical device 20, the recorded insertion values are correlated with the extraction values to ensure minimal trauma or abrasion while the medical device 20 is extracted.

Upon removal of the medical device 20, the extraction process may be performed at the same breathing cycle (same respiratory phase) as the input values recorded for insertion of the medical device 20. Thus ensuring extraction of the medical device 20 with precise accuracy, while accounting for movements in the patient, and eliminating or reducing the incidence of trauma or abrasion.

Figure 6:
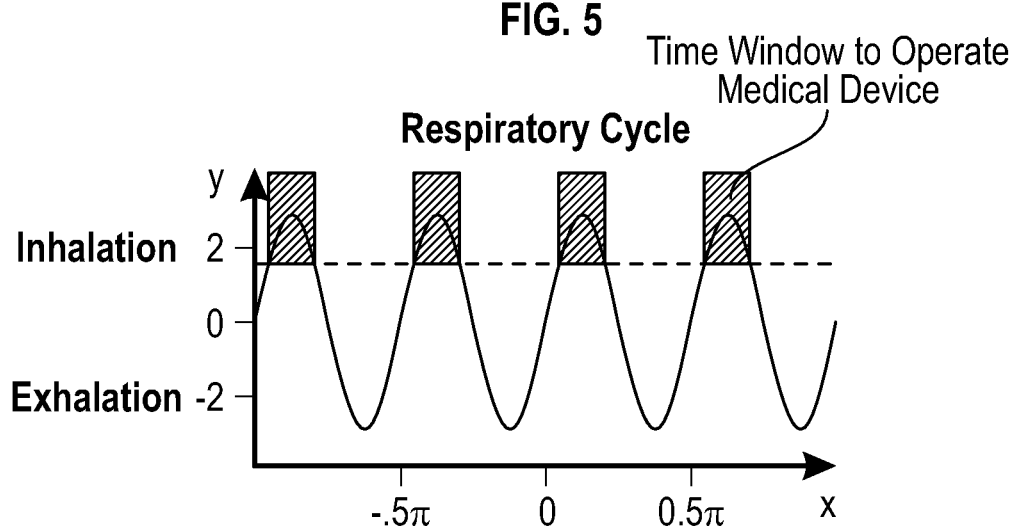
FIG. 6 provides a respiratory cycle of a subject/patient, according to one or more embodiments of the present subject matter.
Figure 7:
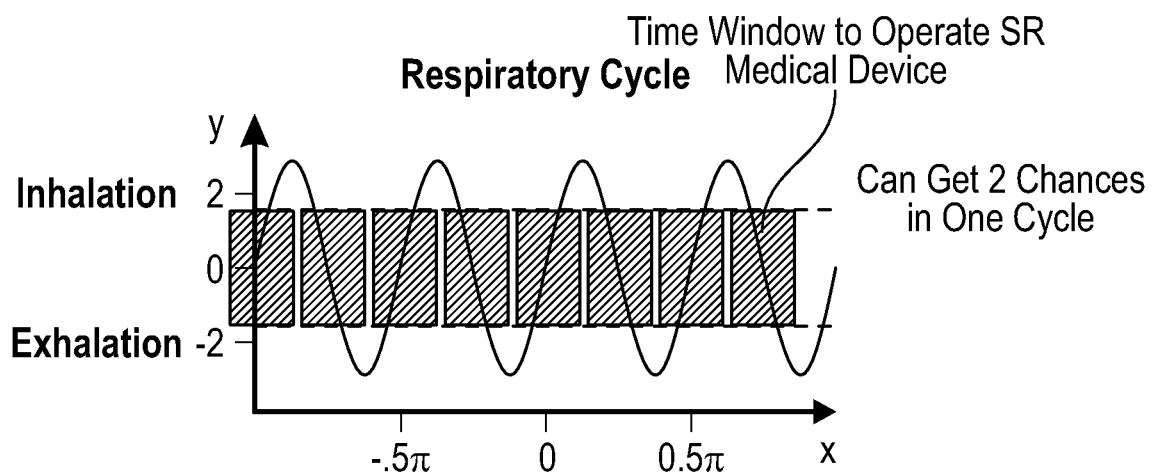
FIG. 7 provides a respiratory cycle of a subject/patient, according to one or more embodiments of the present subject matter.

In various procedures, such as bronchoscopy, the procedure is performed under general anesthesia, so a ventilator 14 controls the breathing of the patient. Accordingly, the controller 12 may receive direct signals of breathing from the ventilator 14 and input to control the medical device 20 from a user interface 16. The controller 12 send the operational signal 18 to control only during one or more specific time window(s) (see FIGS. 6 and 7). As such, the medical device 20 may ignore the operational signal(s) 18 when the operational signal 18 is enacted during the specific time window(s).

In FIG. 2 we see various elements of the subject medical device 10, according to one or more embodiments of the present subject matter. Accordingly, the user interface 16 is in communication with the device controller 12 ("SR controller 12") which communicates with the medical device 20

("SR Robot") which is inserted into the patient. The controller 12 sends operational signals 18 from the user interface 16 to the medical device 20, for enacting the medical device 20 (insertion/extraction/etc). The controller 12 is in further communication with the ventilator 14, or other respiratory equipment, and interprets and/or records the respirator cycle of the patient. If the signal 26 provided by the interface 16 is provided to the controller 12 during a specific time window(s) deemed inappropriate for movement of the medical device 20, the controller 12 ensures the signal 26 is rejected, thus prohibiting movement of the medical device 20.

FIG. 3 provides an exemplary flow chart for operation of the subject medical apparatus 10, according to one or more embodiments of the present subject matter. Under the "insertion" process, the medical device 20 is inserted into the patient, the controller 12 receives signals 26 from the user interface 16 and ventilator 14, and relays an operation signal 18 to the medical device 20. When the controller 12 sends the relayed signal 18 to the medical device 20, the controller 12 records the breathing motion (respiratory cycle), insertion depth of medical device 20, and input angle as a history of the insertion.

In the "extraction" process, detailed in FIG. 3, the recorded information for insertion depth, input angle, and breathing motion, is sent to the controller 12 which receives the signals 26 from the user interface 16 device. The controller 12 checks the current insertion depth, and finds the input angle to send to the medical device 20 based on the recorded history created during insertion. The controller 12 concurrently receive the breathing motion signal from the ventilator 14, and references the current breathing cycle with the historic breathing cycle to match the motion recorded during insertion. If the motions match, the controller 12 facilitates extraction of the medical device 20. If the breathing motions does not match, the controller 12 restricts extraction, and continues to monitor the breathing cycle to identify a match.

In various embodiments, the controller is capable of predicting breathing motion and cycles, based on the recorded history, and may anticipate extraction periods, which may be relayed ahead of time to an end user or physician.

Figure 4:
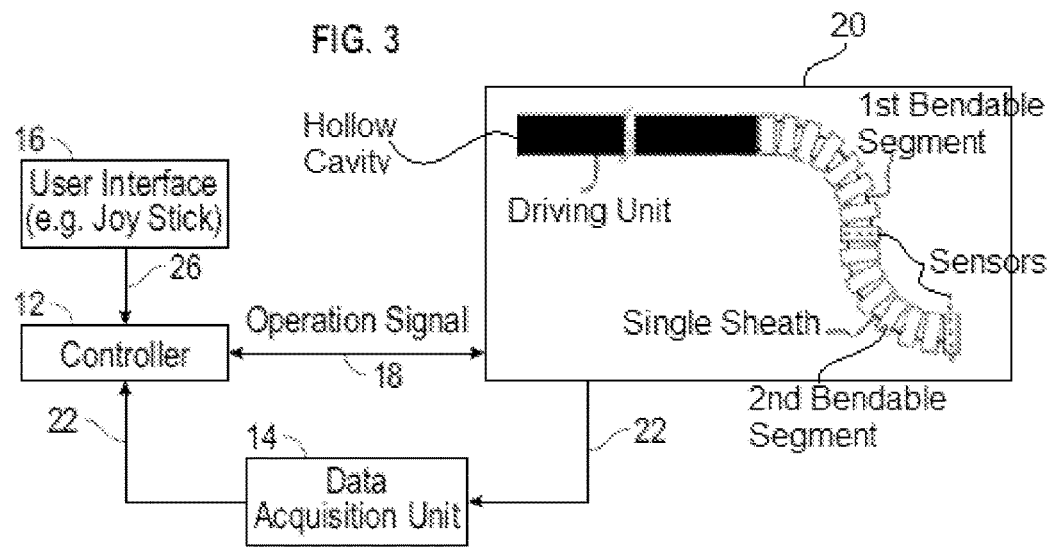
FIG. 4 provides a flow chart of the communication of at least two elements of a medical apparatus, according to one or more embodiments of the present subject matter.

Alternatively or supplemental to the above-referenced recorded history used for extraction, variables in a force measured against time, caused by interaction between the medical device 20 and the airway, may be used to determine the appropriate extraction process. FIG. 4 provides the communication structure of an exemplary medical apparatus 10, according to one or more embodiments of the present subject matter. When the medical device 10 remains at a certain local within the patient, a force 22 caused by interaction between the medical device 20 and the surrounding tissue may be measured and recorded. The force 22 may be periodic, which correlates with breathing motion, as the breathing motion deforms the airway (surrounding tissue), and the deformation exerts a compression force 22 of the medical device 20. Sensors 24 fitted to the medical device 20 can be utilized to measure the force 22 and determine variations in time, which could be correlated to inflation and compression of the lungs, signifying breathing.

A force sensor 24 (not shown) may be attached to the medical device 20, such that when the medical device 20 is inserted into a patient, the controller 12 receives signals from the user interface 16 (e.g. joystick) and a variance force recorded by the force sensor 24 is recorded by the controller 12, via a data acquisition system ("DAQ"), and sent by the operation signal to the medical device 20. When the controller 12 sends a signal to medical device 20, the controller 12 records the force, insertion depth of SR, and input angle as history.

As before, when the medical device 20 is extracted, the controller 12 receives signal from the user interface 16 device. The controller 12 may then check the current insertion depth, and find the input angle to send to the medical device 20, from the history created during insertion based on the current insertion depth. The controller 12 then receive the signal of force from DAQ, and compares it to the current force to determine if there is a match with the force recorded during insertion. If the forces match, the controller 12 sends an operation signal to extract the medical device 20. If the forces do not match, the controller 12 does not send the operation signal to extract the medical device 20, and may continue to monitor the forces to determine an appropriate time for extraction.

Figure 5:
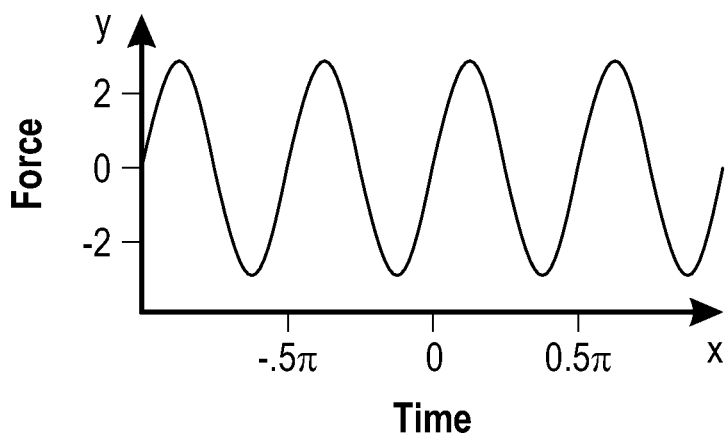
FIG. 5 details a respiratory cycle of a subject/patient, according to one or more embodiments of the present subject matter.

FIG. 5 provides an exemplary breathing cycle for a given patient, wherein the force 22 exerted upon the medical device 20 is recorded again time. The cycles represent an increase of force 22 upon the medical device 20 when a patient inhales in respiration, wherein the decrease of force 22 may indicate exhaling of air by a patient. As can be appreciated, deeper breaths may result in an increase and decrease of force generated by the increase movement of the lungs.

In further embodiments, the controller 12 synchronizes the breathing motion with insertion of the medical device 20. The insertion of medical device 20 is allowed only during a specific time window (e.g. maximum inhalation).

The controller 12 is in communication with a visual monitor which shows the breathing cycle. When the breathing cycle comes to the specified time window of the breathing cycle, the display may changes the color of the monitor in order to signal the user that the medical device 20 may be manipulated safely. In this embodiment, the apparatus 10 may be configured such that the user can always control medical device 20 even outside of the time window (see FIGS. 6 and 7).

In a further embodiment, the controller 12 synchronizes the breathing motion with insertion of the medical device 20. The insertion of medical device 20 may be configured for insertion at a specific time window only (e.g. maximum inhalation). As stated earlier, bronchoscopy is typically done under general anesthesia, so a ventilator 14 controls the breathing of the patient. The ventilator 14 creates the plateau in the breathing cycle around the maximal inhalation, and keeps the shape of the airway consistent. The controller 12 receives breathing signals from the ventilator 14 and signals 26 it to control the medical device 20 from a user interface 16. The controller 12 send the operational signal 18 to control the medical device 20 only during a specific time window. Alternatively, the medical device 20 may be configured to ignore the signal 26 when the signal 26 is relayed outside the specified time window.

Alternatively, the pause in ventilation may be controlled during a different time window. For example, when the physician resumes inserting the medical device 20, the ventilator 14 could pause for a certain amount of time. Presumably, the physician will decide to begin insertion when the airways are in a desirable position, so it would make sense to pause the respiration at this point. The pause should last for as long as the insertion motion is happening, and less than as long as medically acceptable.

The invention claimed is:

1. A medical apparatus comprising:
   a driving unit;
   a single sheath that includes a first bendable segment and a second bendable segment, which are bendable by the driving unit;
   a controller configured to send a control signal to the driving unit for bending at least one of the at least two bendable segments; and
   a device for measuring a movement in a subject,
   wherein the device is in communication with the controller.

2. The medical apparatus of claim 1, further comprising a sensor configured in the single sheath for measuring a value selected from the group consisting of insertion depth, input angle, movement, and force upon the sheath.

3. The medical apparatus of claim 1, wherein the device is in communication with the controller for identifying variations or patterns of movement in the subject.

4. The medical apparatus of claim 1, wherein the device for measuring movement is configured to measure voluntary or involuntary movement in the subject.

5. The medical apparatus of claim 1, wherein the movement measured in the subject is selected from the group consisting of respiration, digestion, blood circulation, and enzyme production/distribution.

6. The apparatus of claim 1, wherein the controller is configured to control the first bendable segment independent of the second bendable segment, while a force is applied from the controller to the second bendable segment via the driving unit in order to maintain a shape of the second bendable segment.

7. The apparatus of claim 1, wherein the first bendable segment and the second bendable segment are configured to independently change a respective bending angle and a respective bending plane in a three dimension space.

8. The apparatus of claim 1, wherein the controller is configured to dislocate from the sheath at a distal end of the sheath.

9. The apparatus for claim 1, wherein the sheath comprises a hollow cavity extending the length of the sheath for insertion of a medical tool.

10. The apparatus of claim 9, where in the medical tool is selected from the group consisting of an endoscopes, a camera, a catheter, clamps, a grasper, scissors, staplers, a needle holder, variations thereof, and derivatives therefrom.

11. A method for treating a subject, comprising:
    Including a medical apparatus comprising:
       a driving unit;
       a single sheath that includes a first bendable segment and a second bendable segment, which are bendable by the driving unit;
       a controller configured to send a control signal to the driving unit for bending at least one of the at least two bendable segments; and
       a device for measuring a movement in a subject,
    inserting the medical apparatus into the subject;
    measuring the movements of a subject while the medical device is inserted into the subject,
    recording the measured movements of the subject, and
    removing the medical apparatus from the subject,
    wherein the recorded measured movements are considered when removing the medical device.

12. The method of claim 11, wherein the medical device further comprises a sensor configured in the single sheath for measuring a value selected from the group consisting of insertion depth, input angle, respiratory phase and force upon the sheath.

13. The method of claim 11, wherein the respiratory device is in communication with the controller for identifying variations or patterns of movement in the subject.

14. The method of claim 11, wherein the device for measuring movement is configured to measure voluntary or involuntary movement in the subject.

15. The method of claim 11, wherein the movement measured in the subject is selected from the group consisting of respiration, digestion, blood circulation, and enzyme production/distribution.

16. The method of claim 11, wherein the controller of the medical device is configured to dislocate from the sheath at a distal end of the sheath.

17. The method of claim 11, wherein the first bendable segment and the second bendable segment of the medical device are configured to independently change a respective bending angle and a respective bending plane in a three dimension space.

18. The method of claim 11, wherein the controller is configured to dislocate the distal end of the single sheath three-dimensionally while keeping a substantially constant orientation of the distal end of the single sheath by bending the first bendable segment and the second bendable segment.

* * * * *